(12) United States Patent
Hickey

(10) Patent No.: US 6,412,639 B1
(45) Date of Patent: Jul. 2, 2002

(54) MEDICAL PROCEDURE KIT HAVING MEDICAL ADHESIVE

(75) Inventor: Timothy P. Hickey, Raleigh, NC (US)

(73) Assignee: Closure Medical Corporation, Raleigh, NC (US)

( * ) Notice: Subject to any disclaimer, the term of this patent is extended or adjusted under 35 U.S.C. 154(b) by 0 days.

(21) Appl. No.: 09/559,651

(22) Filed: Apr. 28, 2000

(51) Int. Cl.⁷ .............................................. B65D 71/00
(52) U.S. Cl. ...................................... 206/570; 206/438
(58) Field of Search .............................. 206/63.5, 229, 206/363, 370, 440, 570–572, 438

(56) References Cited

U.S. PATENT DOCUMENTS

| | | | |
|---|---|---|---|
| 1,009,047 A | * 11/1911 | Capitain | 206/572 |
| 4,194,622 A | 3/1980 | Lewis | |
| 4,522,302 A | 6/1985 | Paikoff | |
| 4,523,679 A | 6/1985 | Paikoff et al. | |
| 4,595,102 A | * 6/1986 | Cianci et al. | 206/572 |
| 4,599,276 A | 7/1986 | Martini | |
| 4,763,791 A | * 8/1988 | Halverson et al. | 206/570 |
| 4,828,113 A | 5/1989 | Friedland et al. | |
| 4,932,552 A | 6/1990 | Wilson | |
| 5,144,942 A | 9/1992 | Decarie et al. | |
| 5,185,001 A | 2/1993 | Galanakis | |
| 5,222,978 A | 6/1993 | Kaplan et al. | |
| 5,282,533 A | 2/1994 | Holzwarth et al. | |
| 5,315,985 A | 5/1994 | Decarie et al. | |
| 5,335,775 A | 8/1994 | Scanlon et al. | |
| 5,344,017 A | 9/1994 | Wittrock | |
| 5,350,060 A | 9/1994 | Alpern et al. | |
| 5,375,717 A | 12/1994 | Roshdy | |
| 5,542,427 A | 8/1996 | Akerfeldt | |
| 5,549,388 A | 8/1996 | Wilkes | |
| 5,590,778 A | 1/1997 | Dutchik | |
| 5,615,766 A | 4/1997 | Gemma, Jr. et al. | |
| 5,645,748 A | 7/1997 | Schiffmann et al. | |
| 5,766,715 A | * 6/1998 | Garconnet | 206/570 |
| 5,853,399 A | * 12/1998 | Sasaki | 206/571 |
| 5,858,303 A | 1/1999 | Schiffmann et al. | |
| 5,860,806 A | 1/1999 | Pranitis, Jr. et al. | |
| 5,868,244 A | 2/1999 | Ivanov et al. | |
| 5,874,044 A | 2/1999 | Kotzev | |
| 5,881,536 A | 3/1999 | Muller-Wille et al. | |
| 5,931,304 A | * 8/1999 | Hammond | 206/570 |
| 5,947,296 A | * 9/1999 | Castora | 206/571 |

FOREIGN PATENT DOCUMENTS

FR   2 668 060 A   4/1992

* cited by examiner

Primary Examiner—Luan K. Bui
(74) Attorney, Agent, or Firm—Oliff & Berridge, PLC (57) ABSTRACT

A medical procedure kit incorporates one or more surgical tools necessary to perform at least part of a medical procedure, along with a container having a quantity of a medical adhesive. Medical adhesives are useful as an alternate or an adjunct to surgical sutures and/or staples in wound closure, as well as for covering and protecting surface wounds such as lacerations, abrasions, burns, stomatitis, sores, minor cuts and scrapes, and other wounds. As such, the inclusion of such an adhesive into a composite medical procedure kit can be of great assistance to a medical doctor or surgeon by providing in single kit form, tools necessary to complete many medical procedures, without having to use multiple procedure kits. The adhesive may be independently sterilized and wrapped from the other surgical tools of the resultant kit, and then associated into kit form, or assembled and sterilized together as a unitary kit. When the adhesive is incompatible with sterilizing procedures of the other components of the kit, the adhesive may be pre-sterilized and protected by a sterilization barrier that shields the adhesive from exposure to the sterilization process used to sterilize other tools of the procedure kit. The adhesive is preferably a 1,1-disubstituted ethylene monomer, such as an alpha-cyanoacrylate.

17 Claims, 10 Drawing Sheets

MEDICAL PROCEDURE KIT HAVING MEDICAL ADHESIVE

BACKGROUND OF THE INVENTION

1. Field of Invention

The invention relates to sterile medical procedure kits.

2. Description of Related Art

Pre-sterilized medical procedure kits are known and used for various medical operating procedures. Such sterilized procedure kits are provided with a plurality of components used in connection with a particular surgical procedure. These kits have been used, for example, as suture or wound closure kits, or other procedural kits, including tools necessary to complete a desired surgical procedure, such as endoscopic or laparoscopic surgery. Such kits include components that must be sterilized before or during packaging and must be maintained in a sterile condition until used.

Sterilization of medical procedure kits and/or its packaging are accomplished by various methods. These methods include chemical, physical, and/or irradiation methods. Examples of chemical methods include exposure to ethylene oxide or hydrogen peroxide vapor. Examples of physical methods include sterilization by heat. Examples of irradiation methods include gamma irradiation, electron beam irradiation, and microwave irradiation.

U.S. Pat. No. 4,522,302 to Paikoff discloses one known pre-sterilized medical procedure kit package within an outer package wrap. The kit includes two compartments, pre-sterilized by ethylene oxide and wrapped within an inner package wrap. A first compartment contains essential medical procedure components, which are subjected to ethylene oxide sterilization. A second compartment contains a vial with an agent incompatible with ethylene oxide sterilization, such as a vial with a rubber stopper. The vial is separately heat sterilized and then sealed inside an ethylene oxide impermeable container and placed in the second compartment prior to exposure of the complete kit to ethylene oxide sterilization.

Another known procedure kit can be found in U.S. Pat. No. 4,523,679 to Paikoff et al., which also discloses a pre-sterilized medical procedure kit with at least two compartments. A larger compartment includes medical components for a particular procedure. A second smaller compartment can have a cavity open from two sides and sealable by barrier layers. In use, the medical components are placed in the larger compartment and the barrier layers are provided on the smaller compartment while the kit is exposed to ethylene oxide sterilization. Then, the kit is removed to a sterile environment and the barrier layers are removed and a second component, made of rubber and heat sterilized elsewhere, is sealed in the smaller compartment with new sterile barrier layers. The package is then placed in a sterile outer wrap and sealed. This allows a kit to include a component that is incompatible with ethylene oxide sterilization.

A known surgical suture kit is commercially available from Inlet Medical Inc. This kit includes a disposable suture passer, a pilot suturing guide, and braided sutures. Such a kit is intended for use in securing trocar wounds made during laparoscopic surgery.

Other suture procedure kits can be found in U.S. Pat. No. 5,350,060 to Alpern; U.S. Pat. No. 5,615,766 to Gemma, Jr. et al.; U.S. Pat. No. 5,335,775 to Scanlon et al.; and U.S. Pat. No. 5,282,533 to Holzwarth et al.

Pre-packaged procedure kits including instrumentation for endoscopic surgery can be found in U.S. Pat. Nos. 5,315,985 and 5,144,942, both to Decarie et al.; and U.S. Pat. No. 5,375,717 to Roshdy. The Decarie et al. patents provide a procedure kit useful in performing laparoscopic or endoscopic surgery, including a trocar assembly, an obturator, a sleeve member, a cutting device, a stapling device, a dissector, a gripping device, a catheter, and the like.

U.S. Pat. No. 5,874,044 to Kotzev discloses sterilization of cyanoacrylate having a package containing the sterile cyanoacrylate. The package is taught to be heat-resistant up to the sterilization temperature, while providing an adequate barrier to moisture and being cyanoacrylate-compatible. The sterilization is achieved using heat sterilization or radiation. Kotzev appears to recognize and teach that cyanoacrylate formulations have reduced shelf life after being exposed to most types of sterilization.

U.S. Pat. No. 5,881,536 to Müller-Wille et al. discloses a method and device for sterile packaging of a substance in a container, whereby the substance is unable to stand the same sterilization process as the one to which the container is subjected. The method includes sterilizing the container (not containing the substance) while the container is enclosed in an outer package so that the container becomes internally and externally sterile; sterilizing the substance with a different sterilizing process; and inserting the substance into the container without contaminating the container or the substance.

Monomer and polymer adhesives are used in both industrial (including household) and medical applications. Included among these adhesives are the 1,1-disubstituted ethylene monomers and polymers, such as the α-cyanoacrylates. Since the discovery of the adhesive properties of such monomers and polymers, they have found wide use due to the speed with which they cure, the strength of the resulting bond formed, and their relative ease of use. These characteristics have made the α-cyanoacrylate adhesives the primary choice for numerous applications such as bonding plastics, rubbers, glass, metals, wood, and, more recently, biological tissues.

It is known that monomeric forms of α-cyanoacrylates are extremely reactive, polymerizing rapidly in the presence of even minute amounts of an initiator, including moisture present in the air or on moist surfaces such as animal (including human) tissue. Monomers of α-cyanoacrylates are anionically polymerizable or free radical polymerizable, or polymerizable by zwitterions or ion pairs to form polymers. Once polymerization has been initiated, the cure rate can be very rapid.

Medical applications of 1,1-disubstituted ethylene adhesive compositions include use as an alternate or an adjunct to surgical sutures and/or staples in wound closure, as well as for covering and protecting surface wounds such as lacerations, abrasions, burns, stomatitis, sores, minor cuts and scrapes, and other wounds. When an adhesive is applied to surfaces to be joined, it is usually applied in its monomeric form, and the resultant polymerization gives rise to the desired adhesive bond.

No known commercial sterilized procedure kits (particularly surgical procedure kits or wound closure kits) include a medical adhesive, such as a 1,1 -disubstituted ethylene monomer (cyanoacrylate). It is believed that this may in part be due to factors involving sterilization. That is, many medical adhesives degrade to below a satisfactory level after multiple exposures to sterilization processes. However, many known procedure kits require multiple sterilization procedures to achieve sterilization of all components within the kit.

SUMMARY OF THE INVENTION

There is a need for a medical procedure kit that includes a medical adhesive useful in connection with at least a portion of a medical or surgical procedure, such as wound closure. The addition of such an adhesive in a surgical kit would greatly benefit the convenience of medical procedures, as adhesive wound closure products, such as Dermabond® adhesive, available from Closure Medical Corporation of Raleigh, N.C. can be readily applied to a wound site and are extremely effective as part of a wound closure system. Such a procedure kit is particularly useful when packaged with a procedure kit for laparoscopic or endoscopic surgery. However, heretofore, such a procedure kit has not been realized in the commercial market.

Applicant has overcome the above and other problems by the present invention, which provides a medical adhesive as part of a sterilized surgical procedure kit.

According to one aspect of the invention, all components of the procedure kit but the adhesive and applicator are packaged in kit form and sterilized. Then, the adhesive and optionally an adhesive applicator are separately sterilized and packaged, with the resultant two sterilized packages being associated so as to provide one convenient, combined medical procedural kit that can be brought into an operating room or other sterile environment to be used.

According to another aspect of the invention, the adhesive and optionally an adhesive applicator are sterilized and placed in a sterilization barrier, such as a foil barrier impervious to a certain type of sterilization procedure, and the sterilization barrier containing the adhesive is provided along with remaining components of the procedure kit in kit form and subsequently exposed to sterilization, such as exposure to ethylene oxide, to sterilize the entirety of the contents. In this embodiment, as the adhesive is contained within the sterilization barrier, the adhesive is not subjected to multiple sterilization processes and thus may prevent possible degradation or polymerization due to over exposure to sterilization processes.

According to yet another aspect of the invention, the adhesive and applicator are placed along with all remaining components into the procedure kit, and are subsequently subjected to one or more sterilization processes. However, in accordance with this aspect, the medical adhesive and applicator are formulated to withstand the applied sterilization process without degradation to below product specification parameters. That is, there is substantially no initiation of polymerization of monomeric liquid adhesive compositions that would substantially affect the utility or shelf-life of the monomer or monomers.

BRIEF DESCRIPTION OF THE DRAWINGS

The foregoing and other features and objects of the invention will become apparent from the following drawings and description, which detail exemplary embodiments of procedure kits, in which.

DETAILED DESCRIPTION OF PREFERRED EMBODIMENTS

Figure 1:
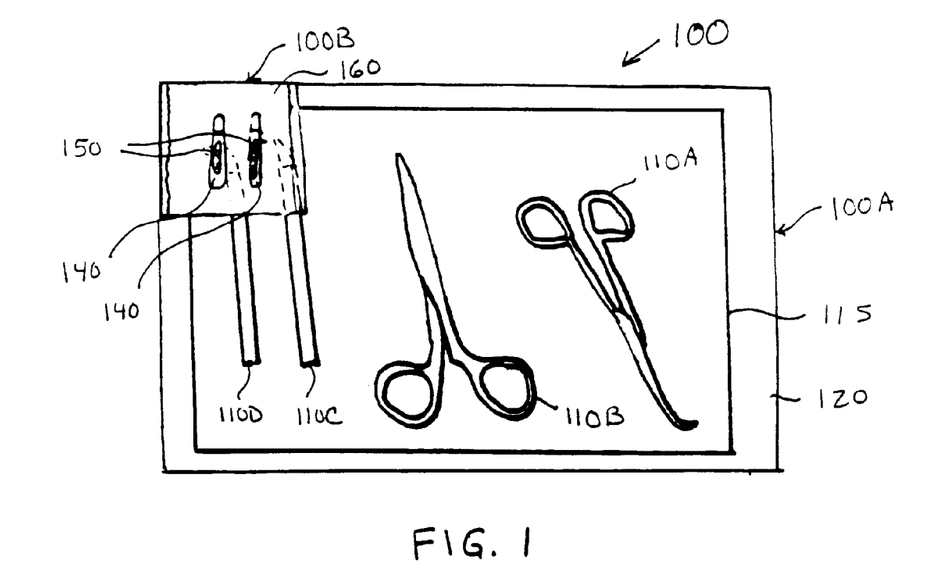
FIG. 1 shows a top view of an exemplary medical procedure kit according to a first embodiment the invention.
Figure 2:
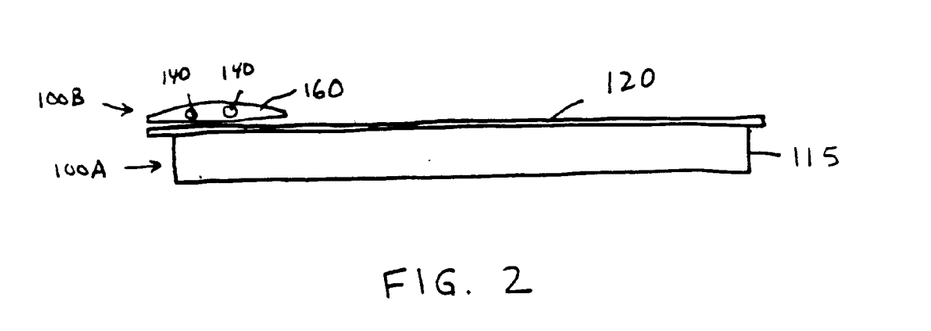
FIG. 2 shows a side view of the procedure kit of FIG. 1.

With reference to FIGS; 1–3, a medical procedure kit 100 according to a first aspect of the invention is provided. The kit 100 shown in FIG. 1 includes a first portion 100A containing one or more surgical or medical tools 110 (tools 110A–110D shown) necessary to perform a particular medical or surgical procedure. This can be most any type of surgical or medical equipment or tools such as, for example, surgical forceps (110A), surgical scissors (110B), and surgical scalpels of various configurations (110C, 110D). Such tools can also tools such as those shown in the procedure kit of FIG. 3, including surgical devices (110E) useful for operating within trocars (110G), obturators (110F), endoscopic wound closure devices (110I, 110H), and applicators and/or parts (110J). Other non-limiting examples of non-illustrated tools include surgical sponges, syringes, anesthetics, needles, clamps, cannulas, vials, gauze pads, swabs, stapling devices, dissectors, and sutures to name a few.

Referring back to FIGS. 1–2, the tool 110 may be provided on a tray 115 and are wrapped or covered by an outer wrap or covering 120. Non-limiting examples of suitable covering materials include Tyvek® (HDPE), paper or PVC film. The covering may be as shown to cover the open top of the tray 115. However, it is also possible for the covering 120 to completely enclose tray 115. In such an embodiment, outer wrap 120 may be in the form of an open-ended tube, with ends being sealed, such as by a heat seal or glue seal, after insertion of the tray and tools within the outer wrap 120. Alternatively, it is possible to have a procedure kit 100 without the tray 115. In such a case, the outer wrap would fully extend around the tools 110 to seal them (similar to that of FIG. 10 only without tray 115).

The kit 100 according to the first embodiment also includes a second portion 100B provided with one or more containers 140 having a medical adhesive 150. The container 140 may be a single-use crushable ampoule or more preferably is an adhesive container/applicator that includes an applicator tip and body for dispensing the adhesive onto a surgical site, such as body tissue. Also, optionally separate applicator(s) and containers with adhesive can be provided. The medical adhesive 150 and container 140 are sealed within a suitable cover 160, which also is preferably formed from Tyvek® (HDPE), paper or PVC film.

The medical adhesive 150 used in any of the embodiments of the invention may include adhesive compositions known in the art or hereafter developed for use in connection with a medical or surgical procedure, including, but not limited to, polymerizable monomeric adhesives. Preferred monomer compositions of the present invention, and polymers formed therefrom, are useful as tissue adhesives, sealants for preventing bleeding or for covering open wounds, and in other biomedical applications. They find uses in, for example, apposing surgically incised or traumatically lacerated tissues; retarding blood flow from wounds; dressing burns; dressing skin or other superficial or surface wounds such as compromised skin or other tissue (such as abrasions, chaffed or raw skin, minor cuts and scrapes, sores and/or stomatitis); protecting intact skin; and aiding repair and regrowth of living tissue.

Preferred monomers that may be used in this invention are readily polymerizable, e.g. anionically polymerizable or free radical polymerizable, or polymerizable by zwitterions or ion pairs to form polymers. Such monomers include those that form polymers, that may, but do not need to, biodegrade. Such monomers and associated adhesive compositions are disclosed in, for example, U.S. Pat. No. 5,328,687; 5,259, 835, 5,624,669, 5,328,687, 5,928,611; 2,721,858; 3,254,111; 4,364,876; 3,554,990; 5,582,834; 5,575,997; 5,514,371; 5,514,372; and 3,940,362, all of which are hereby incorporated by reference herein in their entirety. They are also disclosed in the following co-pending U.S. patent applications Ser. Nos. 09/374,207, 08/609,921, 08/714,288, 08/909, 845, 08/755,007, 08/920,876, 09/025,472, 09/099,457, and 09/471,392, all of which are incorporated by reference herein in their entirety.

A particularly suitable adhesive is a 1,1-disubstituted ethylene adhesive composition. Medical applications of 1,1-disubstituted ethylene adhesive compositions include use as an alternate and an adjunct to surgical sutures and staples in wound closure as well as for covering and protecting surface wounds such as lacerations, abrasions, burns, stomatitis, sores, and other open surface wounds.

Preferred monomers are alkyl alpha-cyanoacrylates and more preferably octyl alpha-cyanoacrylates, especially ethyl butyl or 2-octyl alpha-cyanoacrylate. Monomers used in the present application should preferably be very pure and contain few impurities (e.g., surgical grade).

Referring back to FIGS. 1–3, each individual kit portion (100A, 100B) can be separately assembled and sterilized and then associated into a combined procedural kit form by suitable affixing methods, such as stapling, heat bonding and the like. Another overwrap may optionally be provided to fully enclose both the kit portions (100A, 100B).

Sterilization of the medical adhesive and its packaging can be accomplished by techniques known to the skilled artisan, and is preferably accomplished by methods including, but not limited to, chemical, physical, and/or irradiation methods. Examples of chemical methods include, but are not limited to, exposure to ethylene oxide or hydrogen peroxide vapor. Examples of physical methods include, but are not limited to, sterilization by heat (dry or moist) or retort canning. Examples of irradiation methods include, but are not limited to, gamma irradiation, electron beam irradiation, and microwave irradiation. A preferred method is electron beam irradiation or exposure to ethylene oxide. In embodiments where a composition is to be used for medical applications, the sterilized composition must show low levels of toxicity to living tissue during its useful life.

Figure 4:
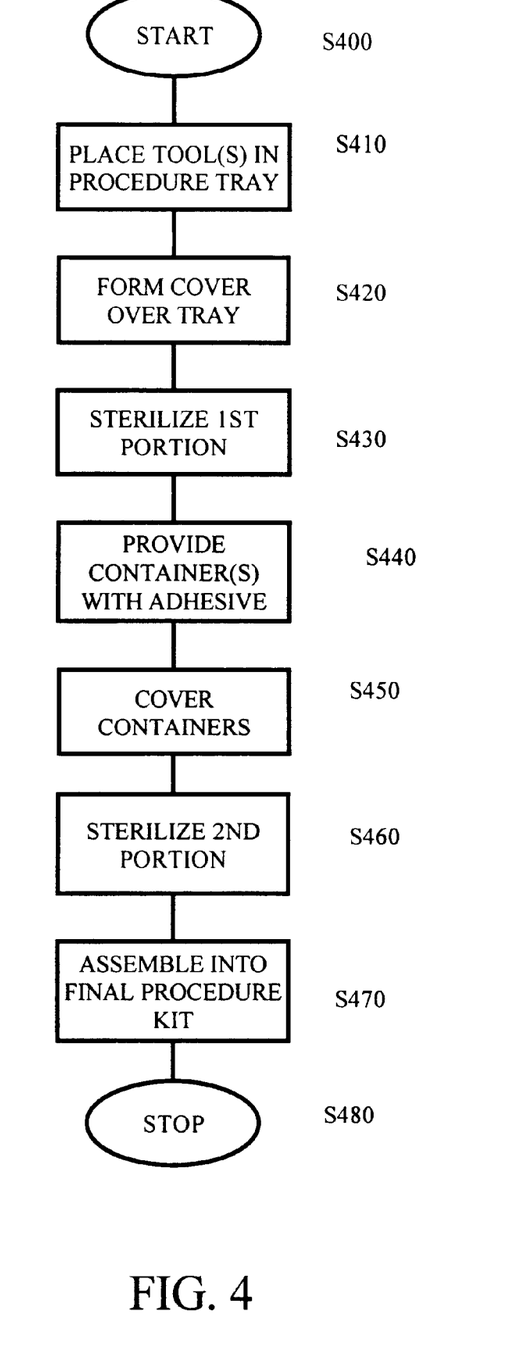
FIG. 4 is a flow chart detailing a sterilization process according to a first embodiment of invention.

An exemplary assembly and sterilization process is shown in FIG. 4. The process starts at step S400 and advances to step S410 where the tray is provided and one or more pre-sterilized tools 110 are placed in the tray. Then at step S420, covering 120 is bonded to tray 115 to provide a sealed enclosure (first portion 100A) housing the tools 110. Then, at step S430, the first portion 100A is subjected to sterilization to sterilize the entire portion 100A and its contents. This may be, for example, by exposure to ethylene oxide or any other suitable sterilization process. In the case of ethylene oxide, the outer covering 120 will be of a material, such as plastic, that allows penetration of the ethylene oxide so as to be able to sterilize the tray 115 and tools 110.

Then, at step S440, one or more containers 140 having a medical adhesive 150 therein are provided, which may be non-sterilized or pre-sterilized. From step S440, flow advances to step S450, where outer covering 160 is provided to fully cover the containers and provide the second kit portion 100B. Covering 160 may be of a plastic material having ends that are heat sealed, glued or otherwise sealed. After step S450, flow advances to step S460 where the second kit portion 100B is sterilized by a sterilization process, such as exposure to ethylene oxide or gamma radiation, although the aforementioned other sterilization methods could alternatively be used. After step S460, flow advances to step S470 where the two kit portions 100A and 100B are affixed to form a final medical procedure kit 100. Suitable affixing can be by numerous methods, such as stapling, heat sealing, gluing, or the like. The final medical procedure kit 100 provides a single kit that contains all essential tools (both tools 110 and adhesive 150) to perform all or at least a particular part of a specified medical procedure. The process then stops at step S480. This kit is convenient to use as only one item needs to be brought into the sterile surgical environment and a surgeon or doctor can have ready access to all equipment necessary to perform a desired procedure.

With this embodiment, the two kit portions 100A, 100B can be assembled and sterilized separately, allowing parallel processing, if desired, and use of differing sterilization procedures. This is important where the medical adhesive 150 is unable to withstand sterilization procedures necessary for sterilization of the other tools, or where multiple sterilization processes would degrade one or more properties of the adhesive.

Figure 5:
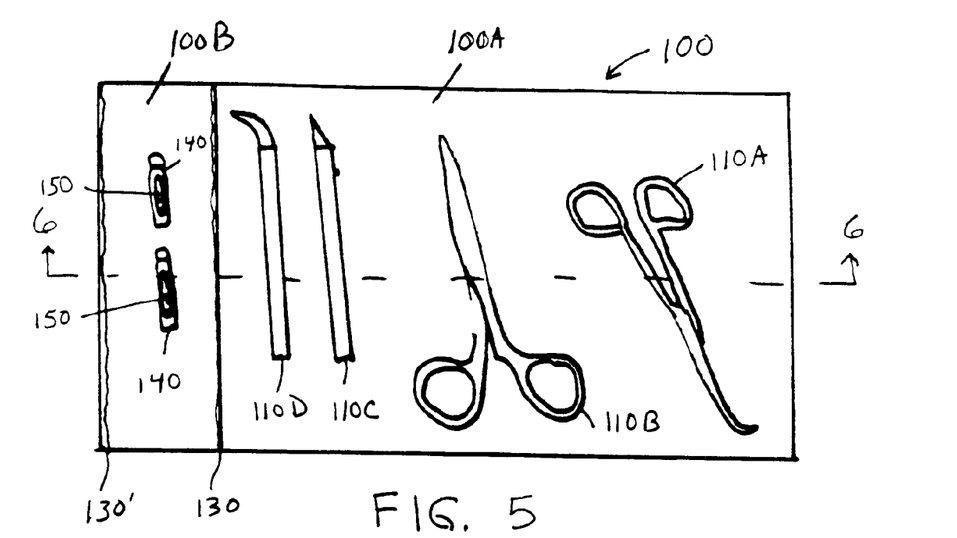
FIG. 5 shows a top view of an exemplary medical procedure kit according to a modified first embodiment of the invention.
Figure 6:
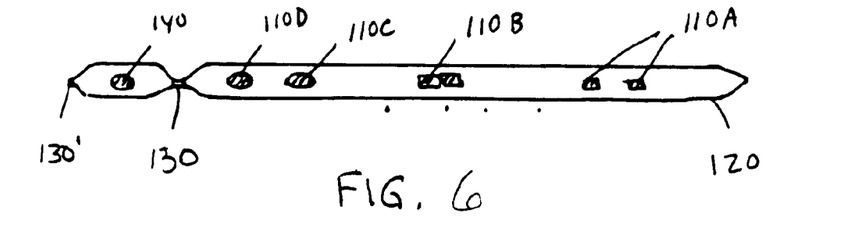
FIG. 6 shows a cross-sectional side view of the procedure kit of FIG. 5 taken along line 6—6.

An alternative arrangement is provided in FIGS. 5–6. In this alternative, the tray 115 is omitted and the tools 110 (110A–110D) are sealed within covering 120. When the medical adhesive 150 is not capable of withstanding multiple sterilization exposure or the particular sterilization process used to sterilize the tools, the tools 110 are sealed in a first portion 110A of the kit and a second portion 110B is initially provided with an open end (far left end). A heat seal or glue seal or other sealing means 130 is provided to separate the kit 100 into the first and second portions. After sterilization of the tools 110 within the first portion 100A, the adhesive 150 within containers 140 can be provided to the second portion 100B and the open end heat sealed, such as by sealing means 130. The entire kit 100 may then be sterilized to sterilize the adhesive, or the containers 140 and adhesive 150 may be pre-sterilized.

Figure 7:
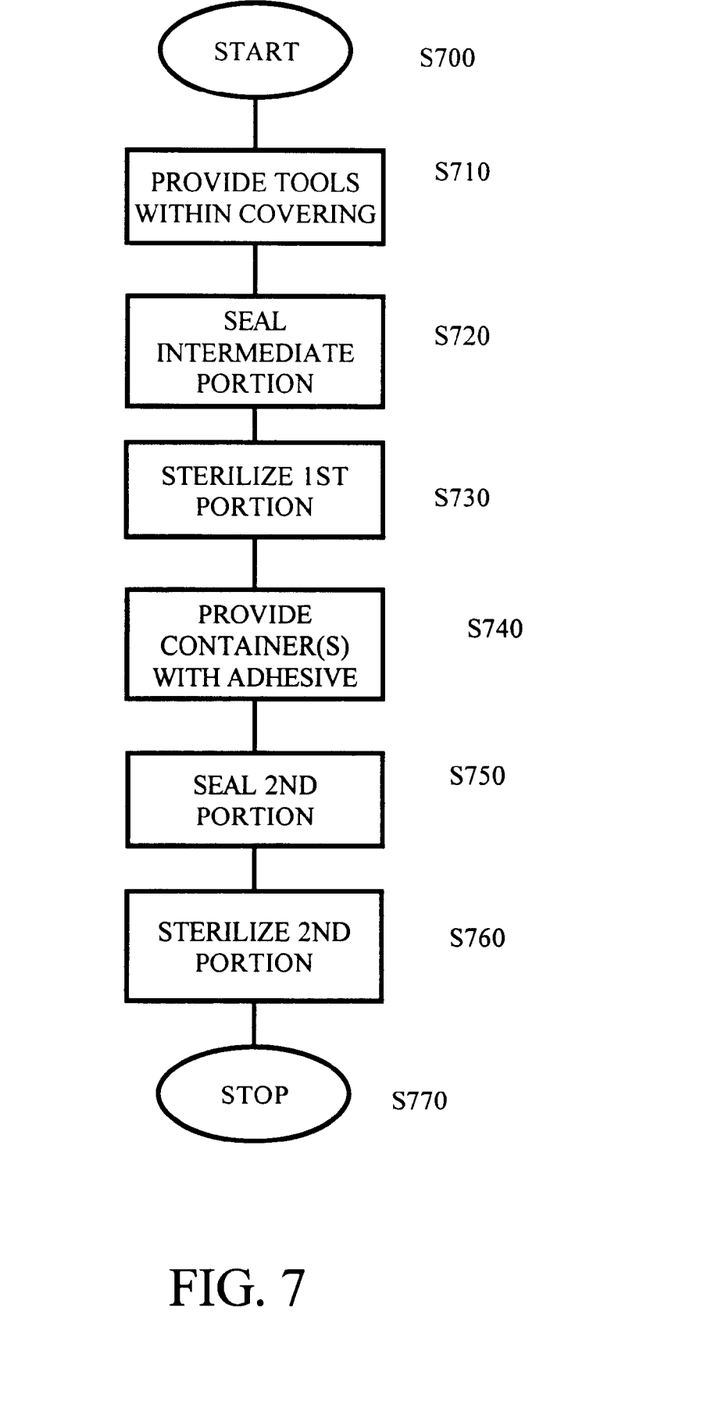
FIG. 7 is a flow chart detailing a sterilization process according to the modified first embodiment of the invention.

A process of assembling and sterilizing the procedure kit 100 according to this modified embodiment is shown in FIG.

7. The process starts at step S700 and advances to step S710 where one or more tools 110 (non-sterilized or pre-sterilized) are provided within outer covering 120. Then at step S720, the covering has an intermediate portion sealed at 130 by a heat seal, glue seal or other sealing method to divide the outer covering into a first portion 100A containing the tools 110 (which is now sealed), and a second portion 100B that is open on one end. Then, at step S730, the first portion 100A is subjected to sterilization to sterilize the entire portion 100A and its contents. This may be, for example, by exposure to ethylene oxide or any other suitable sterilization process. In the case of ethylene oxide, the outer covering 120 will be of a material, such as plastic, that allows penetration of the ethylene oxide so as to be able to sterilize the interior of covering 120 and tools 110.

Then, at step S740, one or more containers 140 having a medical adhesive 150 therein are provided within the second portion 100B. These containers may be non-sterilized or pre-sterilized. From step S740, flow advances to step S750, where the open end of the second portion 100B is sealed by a heat seal or other heat sealing means 130' to fully enclose the containers 140 within the second kit portion 100B. After step S750, flow advances to step S660 where the second kit portion 100B may optionally be sterilized by a sterilization process, such as exposure to ethylene oxide or gamma radiation, although the aforementioned other sterilization methods could alternatively be used. This step may not be necessary if pre-sterilized containers are inserted into the second portion 100B while the kit 100 remains in a sterile environment. After step S760, flow advances to step S770 where the process stops. The final medical procedure kit 100 again provides a single kit that contains all essential tools (both tools 110 and adhesive 150) to perform all or at least a particular part of a specified medical procedure.

Figure 8:
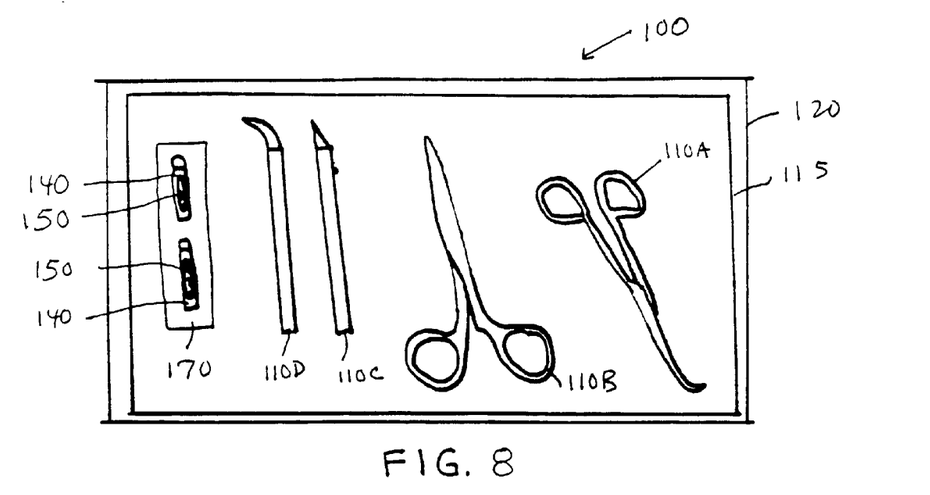
FIG. 8 shows a top view of an exemplary medical procedure kit according to a second embodiment of the invention.
Figure 9:
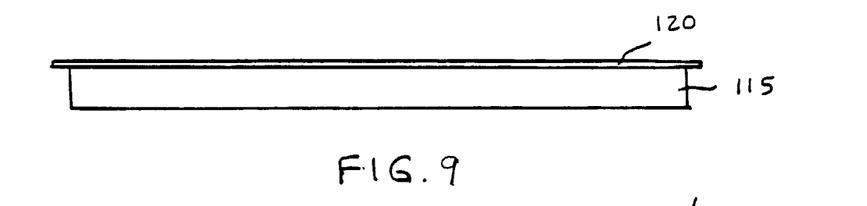
FIG. 9 shows a side view of the procedure kit of FIG. 8.
Figure 10:
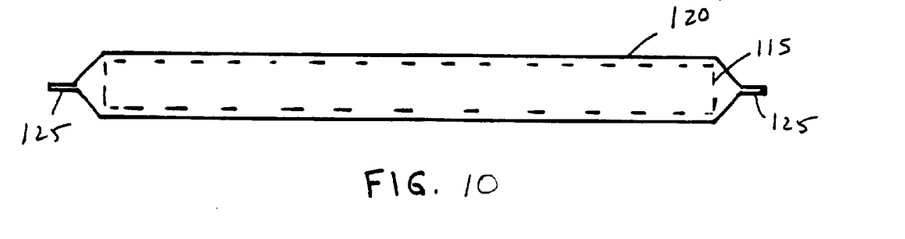
FIG. 10 shows an alternative side view of the procedure kit of FIG. 8.

With reference to FIGS. 8–11, a medical procedure kit 100 according to a second aspect of the invention is provided. The kit 100 rather than providing a first portion and a second portion, instead consists of a single portion containing one or more surgical or medical tools 110 (tools 110A–110D shown) necessary to perform a particular medical or surgical procedure. The tools can be any medical or surgical tool necessary to perform a part of a medical or surgical procedure. The tools 110 may be provided on a tray 115 and are wrapped or covered by an outer wrap or covering 120, which is the same as in the first embodiment. The covering may be as shown to cover the open top of the tray 115. However, it is also possible for the covering 120 to completely enclose tray 115, as shown in FIG. 10. In such an embodiment, outer wrap 120 may be in the form of an open-ended tube, with ends 125 being sealed, such as by a heat seal or glue seal, after insertion of the tray and tools within the outer wrap 120. Alternatively, it is possible to have a procedure kit 100 without the tray 115. In such a case, the outer wrap would fully extend around the tools 110 to seal them (as shown in FIG. 10 only without tray 115).

The kit 100 according to the second embodiment is also provided with one or more containers 140 having a medical adhesive 150, such as, for example, an alph-cyanoacrylate, therein. The container 140 may be a single-use crushable ampoule or more preferably is an adhesive container/applicator that includes an applicator tip and body for dispensing the adhesive onto a surgical site, such as body tissue. In this embodiment, the adhesive 150 or components thereof may be incompatible with sterilization processes necessary to complete sterilization of the remainder of the kit. To accommodate this, the adhesive 150 is pre-sterilized by a suitable sterilization process that does not adversely affect the adhesive and then is packed within or surrounded by a sterilization barrier 170, which seals or provides a protective barrier for the adhesive that protects it from penetration of a particular type of sterilization subsequently used to sterilize the remainder of the kit's contents (i.e., the interior of covering 120 and tools 110). In the case of sterilization by exposure to ethylene oxide, a suitable barrier may be a container or wrap formed from a metal foil, such as aluminum, or a glass or metal container impermeable by ethylene oxide. A metal foil or metal container would also protect against most other sterilization processes as well. The container 140 itself may form protective barrier 170.

In this embodiment, the entire kit 100 can be assembly and sterilized at one time, even if the particular medical adhesive 150 or components thereof are adversely affected by the particular sterilization used as the sterilization barrier 170 protects the adhesive.

Figure 11:
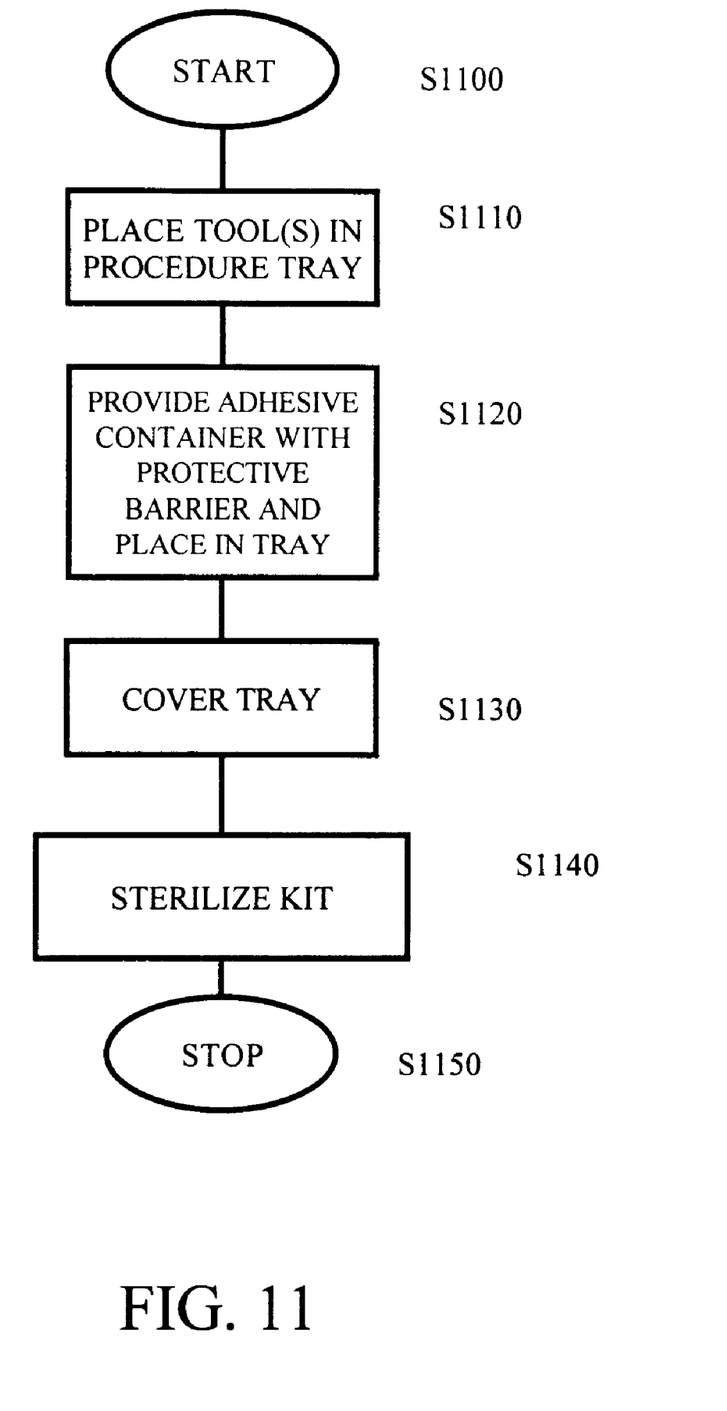
FIG. 11 is a flow chart detailing a sterilization process according to the second embodiment of the invention.

A process of assembling and sterilizing the kit according to the second embodiment will be described with reference to FIG. 11. The process starts at step S1100 and advances to step S1110 where one or more tools 110 are provided within tray 115. Then at step S1120, one or more pre-sterilized containers 140 having a medical adhesive 150 therein are provided with a protective sterilization barrier 170 and placed into the tray 115. Then, at step S1130, covering 120 is formed over tray 115 to seal the tray and provide a sealed enclosure containing the tools and adhesive. From step SI 130, flow advances to step S1140 where the entire kit 100 is subjected to sterilization to sterilize the entire kit and its contents. This may be, for example, by exposure to ethylene oxide or any other suitable sterilization process. In the case of ethylene oxide, the outer covering 120 will be of a material that allows penetration of the ethylene oxide so as to be able to sterilize the interior of covering 120 and tools I 10. However, because of the provision of the sterilization barrier 170, the adhesive is protected from further exposure to the sterilization process. As such, even though the adhesive 150 may be incompatible and adversely affected by the particular sterilization process necessary or desired to sterilize tools 110, adhesive 150 can nonetheless be provided within the same procedure kit. After step S1140, flow advances to step S1150 where the process stops.

Figure 12:
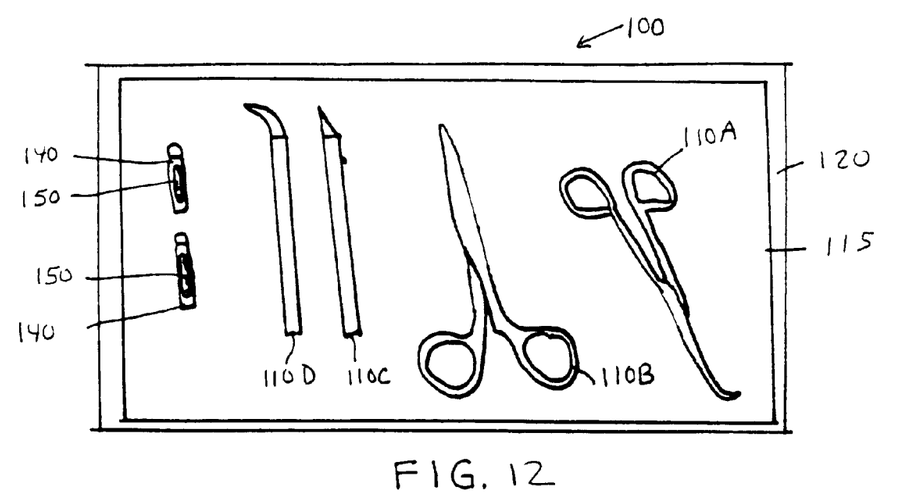
FIG. 12 shows a top view of an exemplary medical procedure kit according to a third embodiment of the invention.
Figure 13:
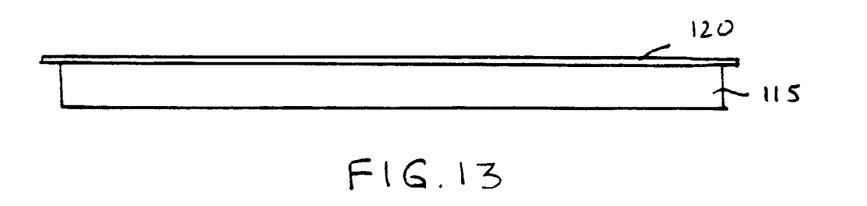
FIG. 13 shows a side view of the procedure kit of FIG. 12.
Figure 14:
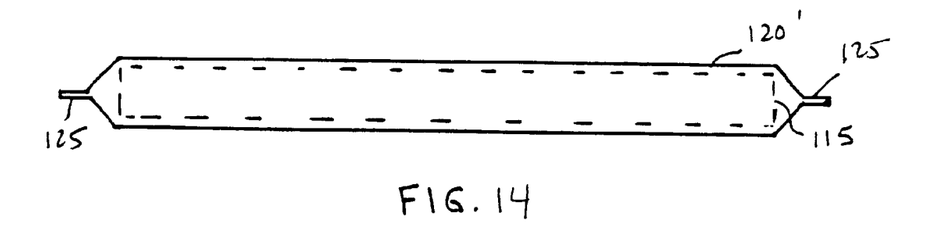
FIG. 14 shows an alternative side view of the procedure kit of FIG. 12.

A third embodiment of the invention will be described with reference to FIGS. 12–15. The kit 100 as in the second embodiment consists of a single portion containing one or more surgical or medical tools 110 (tools 110A–110D shown) necessary to perform a particular medical or surgical procedure. The tool 110 may be provided on a tray 115 and are wrapped or covered by an outer wrap or covering 120, which as in previous embodiments is preferably plastic. The covering may be as shown to cover the open top of the tray 115. However, it is also possible for the covering 120 to completely enclose tray 115, as shown in FIG. 14. In such an embodiment, outer wrap 120 may be in the form of an open-ended tube, with ends 125 being sealed, such as by a heat seal or glue seal, after insertion of the tray and tools within the outer wrap 120. Alternatively, it is possible to have a procedure kit 100 without the tray 115. In such a case, the outer wrap would fully extend around the tools 110 to seal them (as shown in FIG. 14 only without tray 115).

The kit 100 according to the third embodiment is also provided with one or more containers 140 having a medical adhesive 150, such as, for example, an alpha-cyanoacrylate, therein. The container 140 may be a single-use crushable ampoule or an adhesive container/applicator that includes an applicator tip and body for dispensing the adhesive onto a surgical site, such as body tissue. In this embodiment, the adhesive 150 or components thereof are selected to be compatible with sterilization processes necessary to complete sterilization of the remainder of the kit. That is, the adhesive will not degrade below an acceptable amount due to the sterilization process. In this embodiment, the entire kit 100 can be assembly and sterilized at one time.

Figure 15:
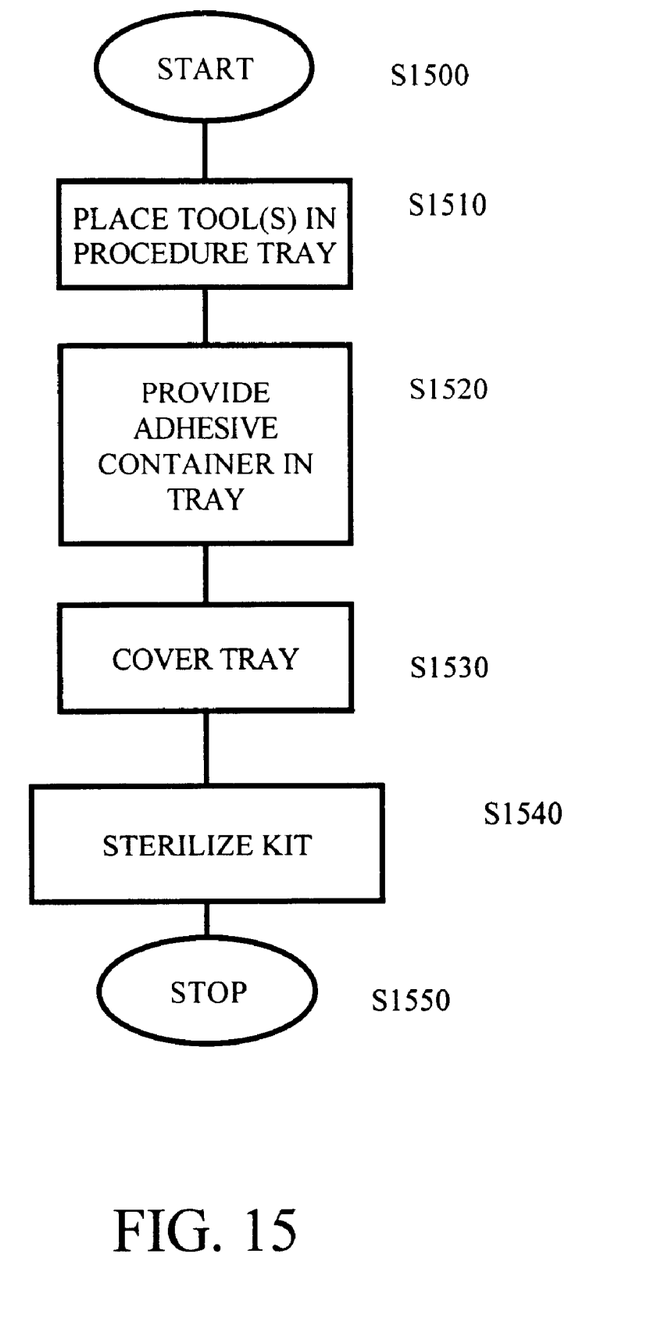
FIG. 15 is a flow chart detailing a sterilization process according to the third embodiment of the invention.

A process of assembling and sterilizing the kit according to the third embodiment will be described with reference to FIG. 15. The process starts at step S1500 and advances to step S1510 where one or more tools 110 are provided within tray 115. Then at step S1520, one or more containers 140 having a medical adhesive 150 therein are placed into the tray 115. Then, at step S1530, covering 120 is formed over tray 115 to seal the tray and provide a sealed enclosure containing the tools and adhesive. From step S1530, flow advances to step S1540 where the entire kit 100 is subjected to sterilization to sterilize the entire kit and its contents. This may be, for example, by exposure to ethylene oxide or any other suitable sterilization process. In the case of ethylene oxide, the outer covering 120 will be of a material, such as plastic, that allows penetration of the ethylene oxide so as to be able to sterilize the interior of covering 120 and tools 110. As the adhesive is selected to have a formulation that withstands exposure to the sterilization process, the entire procedure kit can be sterilized in a single operation. After step S1540, flow advances to step S1550 where the process stops.

Figure 3:
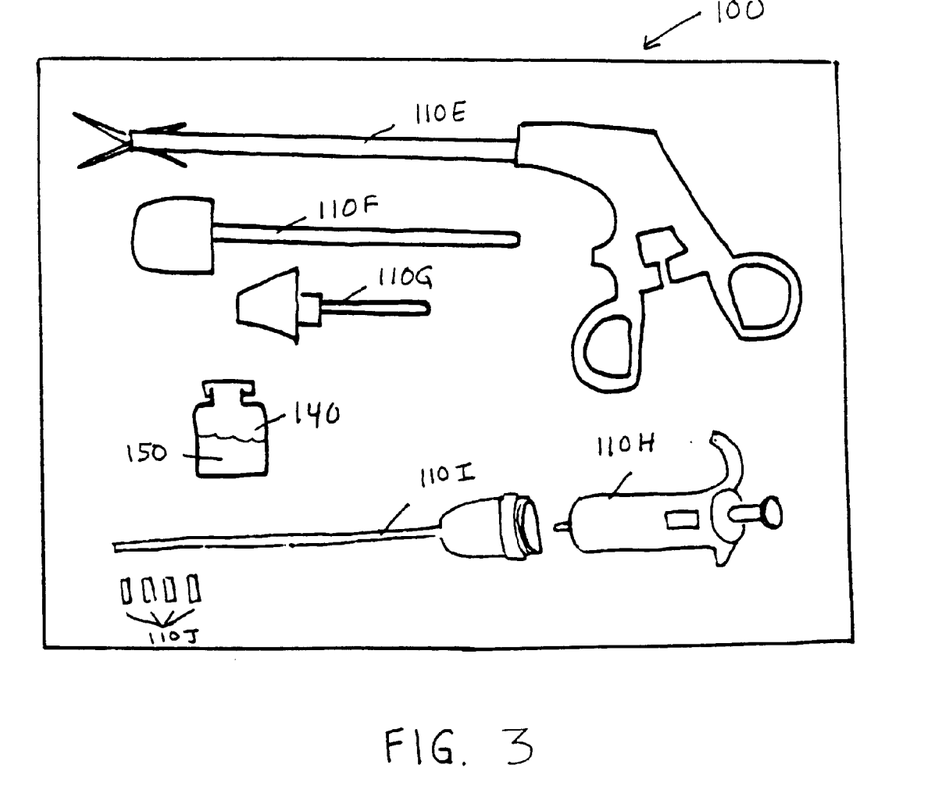
FIG. 3 is an alternative exemplary medical procedure kit, useful in endoscopic or laparoscopic surgery, according to the invention.

The invention is particularly suited towards use as an endoscopic or laparoscopic surgery and recovery procedure kit, a non-limiting example of which is shown in FIG. 3. Kit 100 of FIG. 3 may include, for example, a trocar device 110G, an obturator 110F, a surgical instrument 110E operable through the trocar device to perform laparoscopic or endoscopic surgery, a vial 140 containing a quantity of medical adhesive 150, and a wound closure device (110H, 110I, 110J) used to close an internal wound or tissue site within a body after surgery is complete. An exemplary wound closure device can be found in co-pending U.S. patent application Ser. No. 09/450,686 filed Nov. 30, 1999 entitled "Applicator for Laparoscopic or Endoscopic Surgery", the subject matter of which is incorporated herein by reference in its entirety. Such a wound closure device includes a pump member 110 H, an extension member 1101 extendible through an endoscopic pathway or trocar, and one or more replaceable tips 110J. The tips 110J are placed on the end of extension member 1101 and can be filled with a quantity of adhesive 150 from vial 140 (or prefilled with adhesive, in which case vial 140 may be unneeded). By providing a wound closure device and medical adhesive within an endoscopic medical procedure kit, the entire surgical procedure, including wound closure upon completion can be performed using the tools provided within a single procedure kit. This greatly simplifies the operating room procedure.

Figure 16:
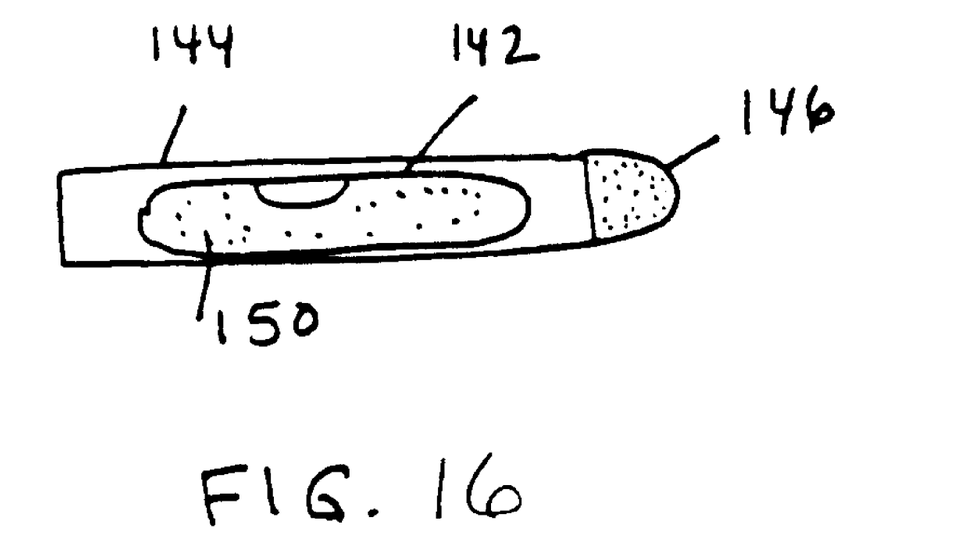
FIG. 16 shows an exemplary applicator/container for use in storing and applying a medical adhesive according to the invention.

The medical adhesive 150 is preferably provided in a container 140 that serves as an applicator/dispenser. An exemplary applicator dispenser 140 will be described with reference to FIG. 16. Preferred embodiments provide a monomer adhesive 150 within a crushable glass ampoule 142, which can serve as container 140. However, it is preferable for the container to provide an applicator function as well. To achieve this, glass ampoule 142 with an adhesive 150 therein may be contained within a flexible applicator body 144, through which the crushable ampoule can be crushed by finger pressure. The applicator body 144 includes a tip 146 that allows dispensing of the adhesive from within applicator body 144 upon crushing of the ampoule. In preferred embodiments of the invention, when the composition is an alpha-cyanoacrylate, the tip 146 may have on or in it a polymerization initiator or rate modifier, e.g., accelerator or inhibitor, which assists the cyanoacrylate adhesive to polymerize quickly and completely as well as allowing the operator to apply the adhesive in several successive layers which will be advantageous for applications requiring high tensile strength. The tip may additionally or alternatively contain a bioactive material. Examples of applicators, applicator tips and dispensers useable in the present invention can be found in U.S. Pat. No. 5,928,611 and co-pending U.S. patent applications Nos. 09/069,979 filed Apr. 30, 1998, 09/176,889 filed October 22, 1998, 09/447,045 filed Nov. 23, 1999, 09/219,851 filed Dec. 23, 1998, 09/430,290 filed Oct. 29, 1999, and 09/385,030 filed Aug. 30, 1999, the disclosures of which are incorporated herein by reference in their entirety.

Various exemplary monomer adhesive formulations were tested for stability and compatibility with single or multiple exposures to various sterilization procedures in order to determine the feasibility of placing medical adhesives into a sterilized procedure kit. The tests used three different sterilization processes: process cycle Q; process cycle R; and process cycle S, which are described below in detail.

Cycle Q uses OXYFUME 2000 (8.6% EO and 91.4% HCFC) as the sterilant. Preconditioning of product prior to sterilization occurs at a relatively high percent relative humidity (70–95%RH) for twelve hours up to six days. Product is then moved into a sterilization chamber, where the validated temperature range of the cycle is not greater than 57° C. Exposure gas dwell time is validated for 3 to 8 hours. After sterilization, the gas is removed from the chamber by allowing the gas to exit through an exhaust system. A vacuum is pulled on the product and then filtered air is injected into the chamber and released to atmospheric pressure. This series of "air rinses" is conducted once.

Cycle R uses 100% ethylene oxide (EO) gas as the sterilant with washes of Nitrogen to remove any oxygen from the sterilization chamber. Pre-conditioning is from 6 to 24 hours at a much lower humidity range than cycle Q (40–57%RH). Sterilization cycle temperature is slightly lower than cycle Q at 43–52° C. Oxygen elimination from the chamber is performed by pulsing nitrogen gas into the chamber a minimum six times and holding for a dwell period of 4 to 6 minutes. After the last pulse of nitrogen gas, an automatic oxygen analyzation instrument checks the oxygen level in the chamber. The oxygen level must pass before the cycle will progress into EO injection. If the oxygen test passes, more nitrogen is added to the chamber at a predetermined pressure, and then EO gas is injected. Gas dwell time is validated for 2 to 3 hours. EO gas is removed from the chamber by exhausting the gas in the chamber through the vent, pulling a deep vacuum, and the injecting nitrogen into the chamber. This nitrogen injection is held for 145 to 155 minutes and then allowed to evacuate through the exhaust system. This is performed a total of twelve times. After the nitrogen flushes, the chamber is released to atmospheric pressure.

Cycle S uses a sterilant comprising 10% EO and 90.0% HCFC. Preconditioning of product prior to sterilization occurs at a relative humidity (40–80%RH) for at least 24 hours, preferably 24–48 hours, at a temperature of between 30–50° C. Product is then moved into a sterilization chamber, where the validated temperature range of the cycle is not greater than 52° C. Exposure gas dwell time is validated for 6 hours and 15 minutes to 6 hours and 45 minutes at a relative humidity of between 45–75% and a pressure between 9.5–11.5 psig. After sterilization, the gas is removed from the chamber by allowing the gas to exit through an exhaust system. A vacuum is pulled on the product (20–24" Hg) six times and then filtered air is injected into the chamber and released to atmospheric pressure. This series of "air rinses" is conducted once at a temperature of between 21–43° C for 12–48 hours.

Table I provides setting times and temperatures for samples of a standard production of (non-sterile) Dermabond® adhesive exposed to a first sterilization cycle (1x), a second sterilization cycle (2x) and a third sterilization cycle (3x) using a same ethylene oxide cycle (R cycle). This test was conducted to establish whether set times and set temperatures would substantially change so as to exceed acceptable standards. The set time of the medical adhesive should be no more than 5 minutes, preferably less than 2.5 minutes, and more preferably less than 2 minutes, or even as low as 1.5 minutes or 1 minute. The medical adhesive will increase its temperature upon setting and preferably should have a set temperature of less than 90° C., more preferably less than 75° C. As the adhesive is preferably topically applied to human tissue during a medical procedure, the set temperature should be chosen to be low enough to prevent a burning or irritation to the tissue. As a result of this testing, it was determined that all lots met acceptable standards, even after exposure to multiple sterilization cycles (up to 3x).

TABLE 1

Setting Time and Setting Temperature for Adhesive Exposed to Sterilization Using The Same Ethylene Oxide Cycle

| | 1X | | 2X | | 3X | |
|---|---|---|---|---|---|---|
| LOT # | Time (sec) | Temp (° C.) | Time (sec) | Temp (° C.) | Time (sec) | Temp (° C.) |
| A | 90 | 35 | 92 | 40 | 133 | 32 |
| B | 92 | 35 | 115 | 32 | 141 | 27 |
| C | 87 | 37 | 114 | 34 | 145 | 25 |
| AVE. | 90 | 36 | 107 | 35 | 140 | 28 |

Table 2 shows the levels of residuals remaining after exposure to 1x, 2x or 3x cycles of ethylene oxide sterilization. Detected residuals on exposed materials after sterilization included ethylene oxide (EO), ethylene chlorohydrin (ECH) and ethylene glycol (EGly). EGly possibly occurs due to hydrolysis of ethylene oxide ($C_2H_4O+H_2O \rightarrow OH-CH_2-CH_2-OH$). ECH possibly occurs due to the reaction of ethylene oxide with chlorine ions ($C_2H_2O+Cl^- \rightarrow OH-CH_2-CH_2-CH_2-Cl$) and/or EGly with HCFC ($OH-CH_2-CH_2-OH+HCFC \rightarrow OH-CH_2-CH_2-Cl$). Acceptable residual amount limits are EO <250 ppm, ECH <250 ppm, and EGly <5000 ppm. As a result of the testing, all lots were found to have acceptable levels of residuals.

TABLE 2

Level of Residuals (EO, ECH and EGly) After Ethylene Oxide Exposures

| LOT# | 1X EO | 1X ECH | 1X EGly | 2X EO | 2X ECH | 2X EGly | 3X EO | 3X ECH | 3X EGly |
|---|---|---|---|---|---|---|---|---|---|
| A | <3 | 10 | 16 | <3 | 6 | 29 | <3 | 5 | 44 |
| B | <3 | 13 | 16 | <3 | 8 | 32 | <3 | 3 | 41 |
| C | <3 | 5 | 16 | <3 | 5 | 29 | <3 | 5 | 41 |
| AVE. | <3 | 10 | 16 | <3 | 6 | 30 | <3 | 4 | 42 |

Table 3 shows set times and set temperatures for adhesive formulations after first (1x), second (2x) and third (3x) cycles of sterilization, again using the same sterilization cycle, in which the concentration of monomer initiators present in the adhesive formulation was varied. In particular, the initiator concentration was increased in 25 ppm increments from samples E to I, up to 280 ppm. The initiator used was a quaternary ammonium salt/acetone mixture. As a result of this testing, it was found that all lots met acceptable standards for set time and set temperature.

TABLE 3

Set Time and Temperature Results for Adhesive With Variable Initiator Concentrations With Exposure to Multiple Ethylene Oxide Cycles

| SAMPLE | 1X Time (sec) | 1X Temp (° C.) | 2X Time (sec) | 2X Temp (° C.) | 3X Time (sec) | 3X Temp (° C.) |
|---|---|---|---|---|---|---|
| E | 133 | 27 | 103 | 25 | 147 | 25 |
| F | 131 | 31 | 144 | 27 | 107 | 27 |
| G | 111 | 30 | 150 | 27 | 150 | 24 |
| H | 101 | 32 | 134 | 32 | 146 | 27 |
| I | 110 | 41 | 127 | 28 | 150 | 25 |

Table 4 shows results of another series of adhesive compositions (lots J, K and L) that were exposed to up to three sterilization processes. This experimental data was generated by exposing a standard production Dermabond® adhesive product to a single ethylene oxide cycle (cycle S). The product from this cycle was then divided and each set was put through a second cycle of either cycle Q or cycle R. This product was then put through a third cycle, which was an identical cycle to the one the product previously went through in the second cycle. The product was sampled after each cycle. This shows that the product can not only be exposed to multiple sterilization cycles, but can be exposed to multiple different cycles and still set in an appropriate timeframe and set temperature.

TABLE 4

Setting Time and Setting Temperature for Adhesive Exposed to Sterilization Using Varied Ethylene Oxide Cycles

| | 1X Cycle S | | 2X Cycle M | | 2X Cycle J | | 3X Cycle M | | 3X Cycle J | |
|---|---|---|---|---|---|---|---|---|---|---|
| Lot# | Time (sec) | Temp (° C.) | Time (sec) | Temp (° C.) | Time (sec) | Temp (° C.) | Time (sec) | Temp (° C.) | Time (sec) | Temp (° C.) |
| J | 46 | 69 | 52 | 64 | 44 | 64 | 65 | 53 | 45 | 60 |
| K | 52 | 51 | 56 | 60 | 48 | 57 | 69 | 45 | 48 | 55 |
| L | 59 | 51 | 68 | 53 | 55 | 50 | 77 | 38 | 58 | 50 |

While the invention has been described with reference to preferred embodiments, the invention is not limited to the specific examples given, and other embodiments and modifications can be made by those skilled in the art without departing from the spirit and scope of the invention.

What is claimed is:

1. A medical procedure kit comprising a saleable package including:

an outer wrap defining at least one sealed and sterile interior portion;

at least one sterilized surgical tool necessary for a particular medical procedure located within said at least one interior portion and sterilized after insertion into the at least one interior portion by a sterilization process that sterilizes both the at least one interior portion and the at least one sterilized surgical tool; and a container having a medical adhesive therein, wherein the adhesive is also sterilized.

2. The medical procedure kit of claim 1, wherein the medical adhesive is a polymerizable monomeric adhesive.

3. The medical procedure kit of claim 2, wherein the monomer is a 1,1-disubstituted ethylene monomer.

4. The medical procedure kit of claim 2, wherein the monomer is an alpha-cyanoacrylate.

5. The medical procedure kit of claim 1, wherein the container includes a crushable ampoule containing the adhesive.

6. The medical procedure kit of claim 5, wherein the kit further includes an adhesive applicator.

7. The medical procedure kit of claim 6, wherein the adhesive container comprises the adhesive applicator.

8. The medical procedure kit of claim 1, wherein said at least one sterilized surgical tool and said container are within the same interior portion of said at least one outer wrap.

9. The medical procedure kit of claim 8, wherein said at least one sterilized surgical tool and said container have been sterilized during a same sterilization process.

10. The medical procedure kit of claim 8, further comprising a sterilization barrier surrounding said adhesive, said sterilization barrier being impervious to a sterilization process used to sterilize said at least one sterilized surgical tool.

11. The medical procedure kit of claim 10, wherein said container acts as said sterilization barrier.

12. The medical procedure kit of claim 10, wherein said sterilization barrier is impervious to ethylene oxide sterilization.

13. The medical procedure kit of claim 10, wherein said sterilization barrier is one of a metal foil and glass.

14. The medical procedure kit of claim 1, wherein said at least one sterilized surgical tool and said container are located within different interior portions.

15. The medical procedure kit of claim 13, wherein said at least one sterilized surgical tool and said container have been sterilized separately.

16. The medical procedure kit of claim 1, wherein two separate outer wraps are provided, one containing said at least one sterilized surgical tool and the other containing said container with said adhesive, both outer wraps being affixed to one another.

17. The medical procedure kit of claim 1, wherein the at least one sterilized surgical tool forms part of a wound closure system.

* * * * *